US008536330B2

(12) United States Patent
Pandya et al.

(10) Patent No.: US 8,536,330 B2
(45) Date of Patent: Sep. 17, 2013

(54) INTERMEDIATES FOR THE PREPARATION OF HMG-COA REDUCTASE INHIBITORS

(75) Inventors: Vishwesh Pravinchandra Pandya, Jamnagar (IN); Santosh Richhariya, Sagar (IN); Prabhakar Divya, Nadendla (IN); Hashim Nizar Poovanathil Nagoor Meeran, Pathanamithitta (IN); Neera Tewari, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 13/642,209

(22) PCT Filed: Apr. 21, 2011

(86) PCT No.: PCT/IB2011/051757
§ 371 (c)(1),
(2), (4) Date: Feb. 21, 2013

(87) PCT Pub. No.: WO2011/132172
PCT Pub. Date: Oct. 27, 2011

(65) Prior Publication Data
US 2013/0150579 A1  Jun. 13, 2013

(30) Foreign Application Priority Data

Apr. 23, 2010  (IN) .............. 980/DEL/2010

(51) Int. Cl.
*C07D 417/12* (2006.01)
(52) U.S. Cl.
USPC ......................... 544/297; 544/335
(58) Field of Classification Search
None
See application file for complete search history.

(56) References Cited

U.S. PATENT DOCUMENTS 5,260,440 A   11/1993  Hirai et al. .................. 544/322

OTHER PUBLICATIONS

Greene, T.W. and Wuts, P.G.M., 2007. *Protective Groups in Organic Synthesis*. 4th Edition. New York: Wiley Interscience Publications.
Carey and Sundberg, 2007. *Advanced Organic Chemistry. Part B: Reactions and Synthesis*. 5th Edition. New York:Springer Science+Business Media, LLC, Chapter 3.
Ahmad et al., "(3R,5S,E)-7-(4-(4-Fluorophenyl)-6-isopropyl-2-(methyl(1-methyl-1H-1,2,4-triazol-5-yl)amino)pyrimidin-5-yl)-3,5-dihydroxyhept-6-enoic Acid (BMS-644950): A Rationally Designed Orally Efficacious 3-Hydroxy-3-methylglutaryl Coenzyme-A Reductase Inhibitor with Reduced Myotoxicity Potential", *Journal of Medicinal Chemistry*, 51(9):2722-2733 (2008).
Aissa, "Mechanistic Manifold and New Developments of the Julia-Kocienski Reaction", *European Journal of Organic Chemistry*, 2009(12):1831-1844 (2009).

*Primary Examiner* — Andrew D Kosar
*Assistant Examiner* — John S Kenyon

(57) ABSTRACT

The present invention provides a process for preparing novel intermediates of Formula wherein, $R^1$ can be hydrogen, $C_1$-$C_4$ alkyl, halogen, nitro, hydroxy, or $C_1$-$C_4$ alkoxy; $R^x$ can be selected from hydrophobic residue of HMG-CoA reductase inhibitors; which can be effectively used for the preparation of HMG-CoA reductase inhibitors such as rosuvastatin and pharmaceutically acceptable salts thereof.

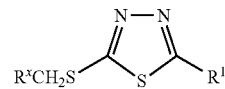

Formula IV

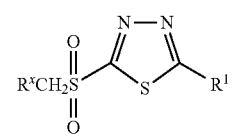

Formula V

15 Claims, No Drawings

1

INTERMEDIATES FOR THE PREPARATION OF HMG-COA REDUCTASE INHIBITORS

FIELD OF THE INVENTION

The present invention provides a process for preparing novel intermediates of Formulae

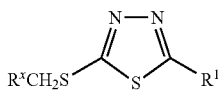

Formula IV

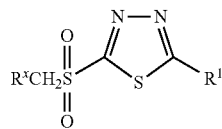

Formula V wherein, $R^1$ can be hydrogen, $C_1$-$C_4$ alkyl, halogen, nitro, hydroxy, or $C_1$-$C_4$ alkoxy; $R^x$ can be selected from hydrophobic residue of HMG-CoA reductase inhibitors, which can be effectively used for the preparation of HMG-CoA reductase inhibitors such as rosuvastatin and pharmaceutically acceptable salts thereof.

BACKGROUND OF THE INVENTION

HMG-CoA reductase inhibitors are the compounds which play a main role in the synthesis of cholesterol, and subsequently they suppress the biosynthesis of cholesterol. Therefore, they are useful in the treatment of hypercholesterolemia, hyperlipoproteinemia, and atherosclerosis Rosuvastatin calcium (Crestor®) is chemically known as bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid], calcium salt.

Rosuvastatin was first disclosed in U.S. Pat. No. 5,260,440, which also discloses the process for the synthesis of rosuvastatin calcium.

Several processes have been reported in literature for the preparation of rosuvastatin, such as WO 2004/014872, WO 2004/108691, WO 2005/042522, WO 2005/054207, WO 2005/077916, WO 2006/035277, WO 2007/041666, WO 2007/125547 or WO 2008/044243.

There remains a need in the art for processes for preparing rosuvastatin which are cost effective, have fewer purification steps, are suitable for industrial scale preparation, result in high yields and are environmentally friendly.

SUMMARY OF THE INVENTION

The present invention provides a process for preparing novel intermediates of Formulae

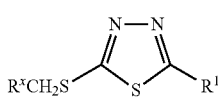

Formula IV

-continued

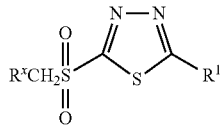

Formula V wherein, $R^1$ can be hydrogen, $C_1$-$C_4$ alkyl, halogen, nitro, hydroxy, or $C_1$-$C_4$ alkoxy; $R^x$ is a hydrophobic residue of HMG-CoA reductase inhibitors including, for example:

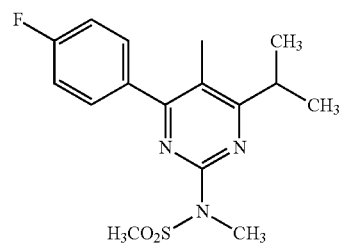

Formula A

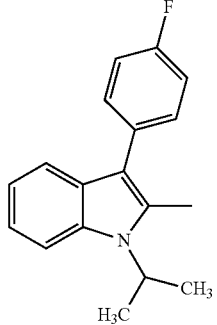

Formula B

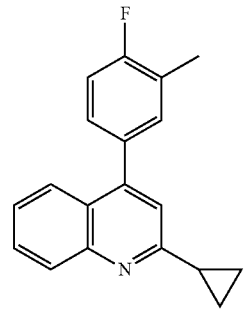

Formula C which can effectively be used for the preparation of HMG-CoA reductase inhibitors such as rosuvastatin and pharmaceutically acceptable salts thereof.

One aspect of the present invention provides a process for preparing novel intermediate of Formula IVa [Formula IV when $R^x$ is Formula A]

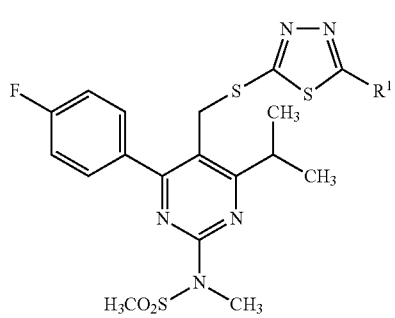

Formula IVa wherein, $R^1$ can be hydrogen, $C_1$-$C_4$ alkyl, halogen, nitro, hydroxy, or $C_1$-$C_4$ alkoxy.

The process comprises the steps of:

(a) converting a compound of Formula Ia

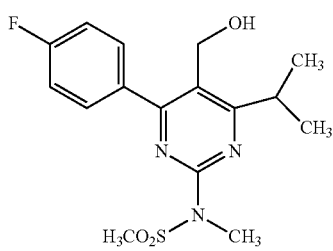

Formula Ia to a compound of Formula IIa,

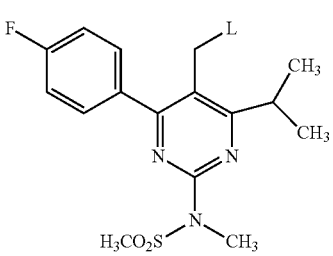

Formula IIa wherein, L is a leaving group;

(b) reacting a compound of Formula IIa with a compound of Formula III

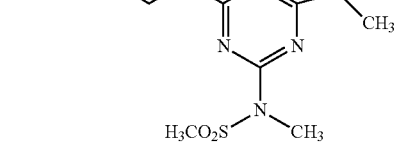

Formula III to give a compound of Formula IVa,

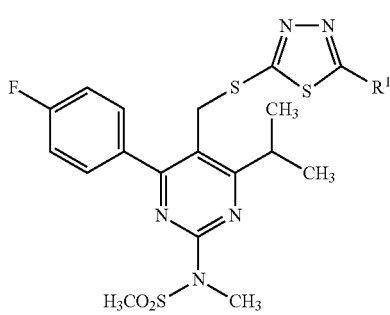

Formula IVa wherein, $R^1$ is same as defined above.

Another aspect of the present invention provides a process for the preparation of a compound of Formula Va [Formula V when $R^x$ is Formula A]

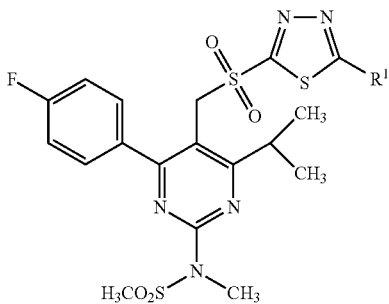

Formula Va wherein, $R^1$ is as defined above.

The process comprises the steps of:

(a) converting a compound of Formula Ia

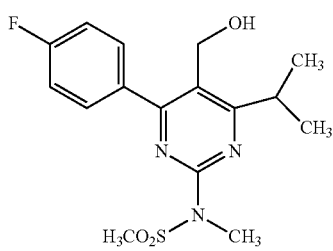

Formula Ia to a compound of Formula IIa,

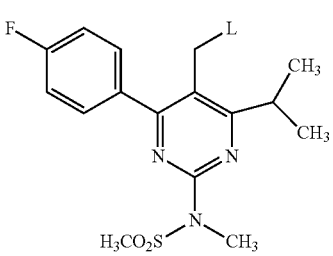

Formula IIa wherein, L is a leaving group;

(b) reacting a compound of Formula IIa with a compound of Formula III

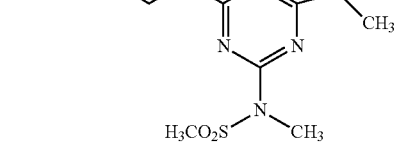

Formula III to give a compound of Formula IVa,

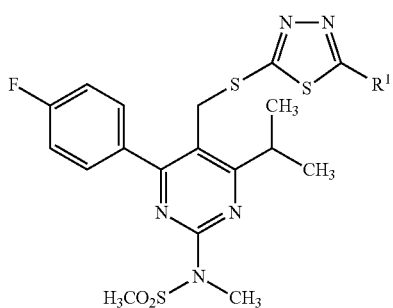

Formula IVa wherein, $R^1$ is same as defined above;

(c) oxidizing a compound of Formula IVa to a compound of Formula Va.

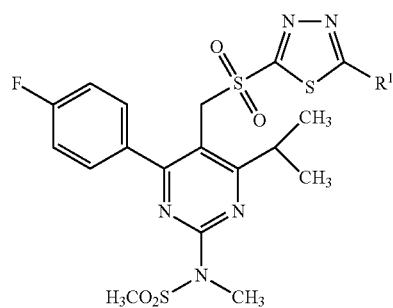

Formula Va

Another aspect of the present invention provides a compound of Formula IVa and a compound of Formula Va.

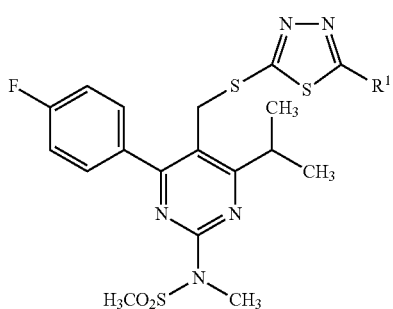

Formula IVa

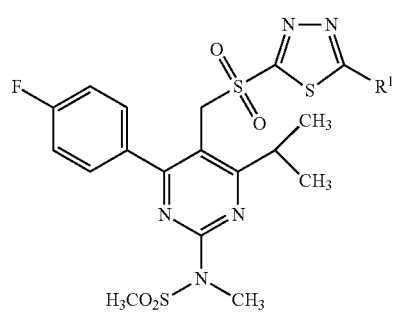

Formula Va

Another aspect of the present invention provides use of an intermediate of Formula IVa or Formula Va, for preparing rosuvastatin or pharmaceutically acceptable salts thereof.

Yet another aspect of the present invention provides a process for the preparation of rosuvastatin calcium having the following formula:

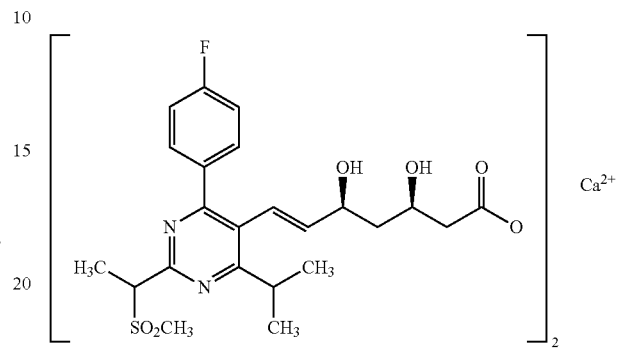

the process comprises the steps of:

(a) converting a compound of Formula Ia

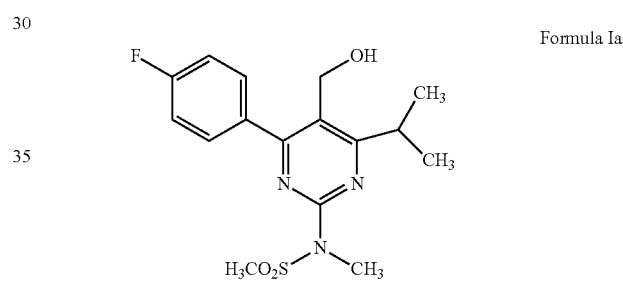

Formula Ia to a compound of Formula IIa;

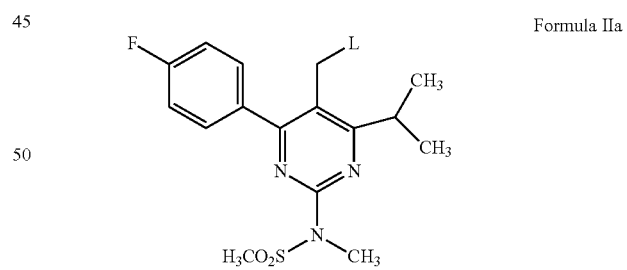

Formula IIa wherein, L is a leaving group;

(b) reacting a compound of Formula IIa with a compound of Formula III

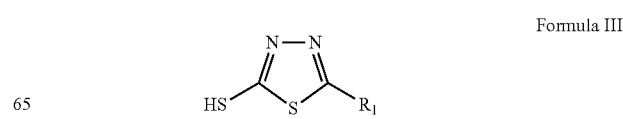

Formula III to give a compound of Formula IVa

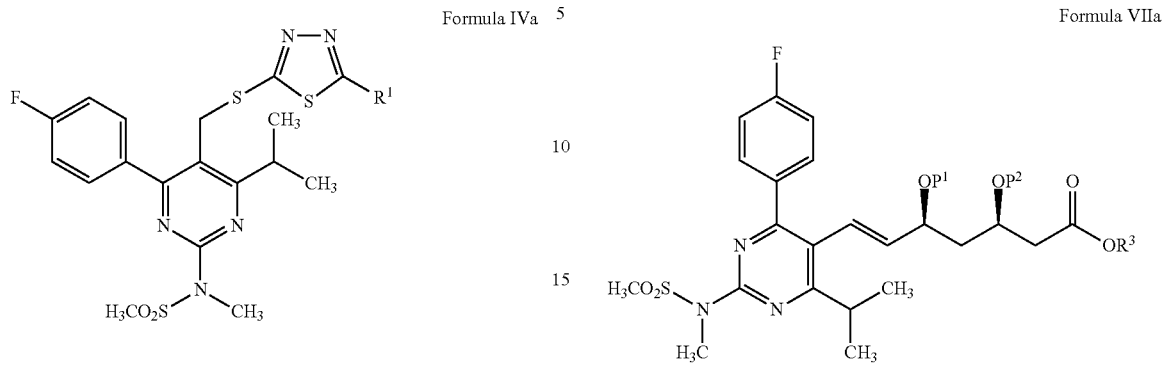

Formula IVa wherein, R¹ is same as defined above;

(c) oxidizing a compound of Formula IVa to a compound of Formula Va;

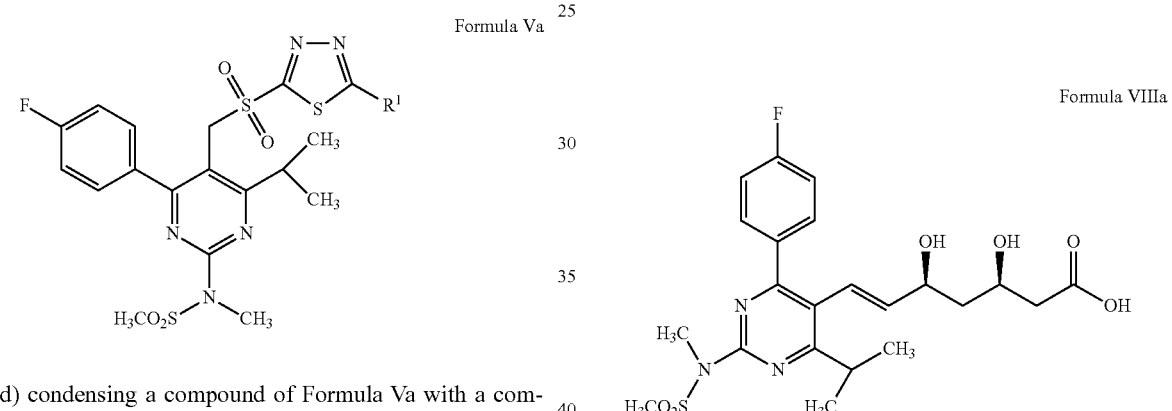

Formula Va (d) condensing a compound of Formula Va with a compound of Formula VI,

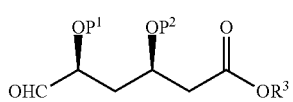

Formula VI wherein, R³ can be hydrogen, alkyl, cycloalkyl, arylalkyl, aryl or carbonylbenzyloxy (cbz), preferably alkyl, more preferably, tertiary butyl; P¹ and P² can be hydrogen or a protecting group wherein, preferably P¹ and P² combines to form structure represented as

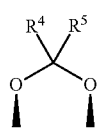

wherein, R⁴ and R⁵ can be alkyl group, alkoxy group or can combine together to form a cyclic hydrocarbon chain or a carbonyl group, to give a compound of Formula VIIa Formula VIIa wherein, P¹, P² and R³ are as defined above;

(e) de-protecting or hydrolyzing a compound of Formula VIIa to give a compound of Formula VIIIa;

Formula VIIIa (f) converting a compound of Formula VIIIa to an amine salt; and (g) converting an amine salt of a compound of Formula VIIIa to rosuvastatin calcium.

According to yet another aspect of the present invention there is provided a pharmaceutical composition comprising:

a) rosuvastatin calcium of Formula

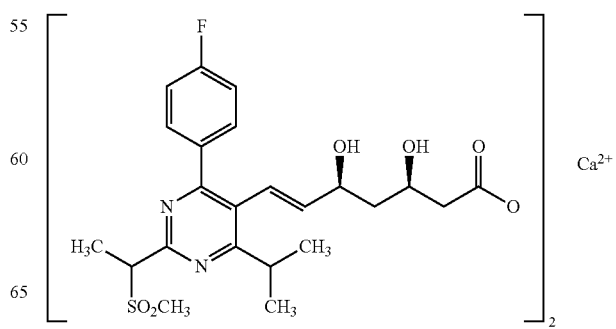

b) one or more compounds selected from

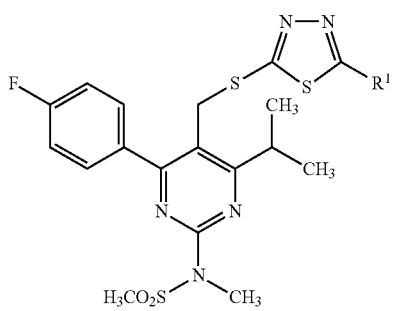

Formula IVa

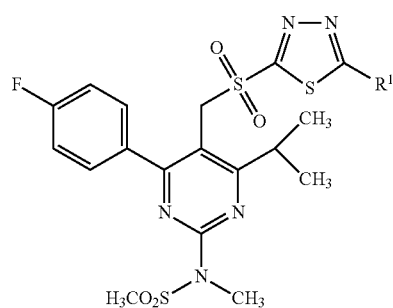

Formula Va wherein, $R^1$ is as defined above.

Compounds listed in component (b) may be present in amounts up to 2% by weight with respect to the total weight of components (a) and (b) when determined by HPLC. Preferably, compounds listed in component (b) may be present in amounts 0.2% by weight. The compound in component (a), i.e., the active ingredient is preferably present in amounts greater than 95% by weight, preferably greater than 98%, and more preferably in amounts greater than 99% with respect to the total weight of components (a) and (b) when determined by HPLC.

According to yet another aspect of the present invention, there is provided rosuvastatin calcium, prepared according to the process described above, wherein rosuvastatin calcium has purity of more than 99.0% and compounds of Formula IVa and Formula Va are present in amounts less than 0.10%. Preferably, rosuvastatin calcium has purity of more than 99.5% when determined by HPLC and the compounds of Formula IVa and Formula Va are present in amounts less than 0.05%.

Other objects, features, advantages and aspects of the present invention will become apparent to those of ordinary skill in the art from the following detailed description.

DETAILED DESCRIPTION OF THE INVENTION

As used herein, "pharmaceutically acceptable salts" refers to the addition salts using cations capable of forming such salts. The term "a cation capable of forming a pharmaceutically acceptable salt" refers to alkali metal ion (e.g., lithium, sodium, potassium or cesium), alkaline earth metal ion (e.g., beryllium, magnesium or calcium), ammonium ion or amine salts (e.g., methyl amine, ethyl amine, n-propyl amine, isopropyl amine, n-butyl amine, tertiary butyl amine, or the like). The pharmaceutically acceptable salts can be crystalline, semi crystalline, or amorphous in nature.

As used herein, "alkyl group" refers to straight, branched, or cyclic hydrocarbon, (e.g., methyl, ethyl, n-propyl, isopropyl, cyclopropyl, n-butyl, isobutyl, sec-butyl, tert-butyl, cyclobutyl, n-pentyl, isopentyl, neopentyl, tert-pentyl, cyclopentyl, n-hexyl, isohexyl or the like). "Halogen" means fluorine, chlorine, bromine and iodine.

As used herein, room temperature is meant to indicate a temperature range of about 25° C. to about 35° C.

As used herein, the term "protecting group" refers to hydroxyl protecting groups described in *Protective Groups in Organic Synthesis* by Greene and Wuts or *Protecting Groups* by Carey and Sundberg. The preferred hydroxyl protecting groups are ethers (e.g., methyl ether, methoxy methyl ethers, methoxyethoxymethyl ethers, methyl thiomethyl ethers, benzyloxymethyl ethers, tetrahydropyranyl ether, ethoxyethyl ethers, benzyl ethers, 2-naphthyl ethers, p-methoxybenzyl ethers, o-Nitrobenzyl ethers, p-Nitobenzyl ethers, trityl ethers, trimethyl silyl ethers, triethyl silyl ethers, triisopropyl silyl ethers, phenyl dimethyl silyl ethers or t-butyldimethylsilyl ethers), acetonides (isopropylidenes), cycloalkylidene ketals or benzylidene acetals (e.g., p-methoxybenzylidenes, or the like).

The hydroxyl group of the compound of Formula Ia can be displaced by a suitable leaving group to give a compound of Formula IIa using the procedures known to a person of ordinary skill in the art. For example, the reaction can be carried out in the presence of a base in a solvent. A suitable leaving group can be defined as a group which can be easily displaced by the reaction with an appropriate reagent. A suitable leaving group includes halo (e.g., bromo, chloro, or the like), alkyl sulphonyloxy (e.g., methylsulphonyloxy, trifluoro methylsuphonyloxy, or the like), aryl suphonyloxy (e.g., benzyl suphonyloxy, p-tolyl suphonyloxy, or the like), phosphate (e.g., diphenyl phosphate, or the like) or phosphite (diphenyl phosphate, or the like). The solvent can be selected from halogenated solvents (e.g., dichloromethane, chloroform, carbon tetrachloride, or the like), ketones (e.g., acetone, 2-butanone, methyl isobutyl ketone, methyl ethyl ketone, or the like), esters (e.g., ethyl acetate, methyl acetate, tertiary butyl acetate, or the like), nitriles (e.g., acetonitrile or the like), aprotic polar organic solvents (e.g., dimethyl formamide, dimethyl sulfoxide, dimethyl acetamide, or the like). The base can be selected from organic base (e.g., triethylamine, diisopropylethylamine, diisopropylamine, pyridine, dimethylaminopyridine, or the like), inorganic base (e.g., sodium hydroxide, potassium hydroxide, sodium carbonate, potassium carbonate, sodium bicarbonate or potassium bicarbonate), or a mixture thereof.

A compound of Formula IIa can be reacted with a compound of Formula III, (wherein, $R^1$ is as defined above, preferably methyl) to give a compound of Formula IVa. The reaction can be carried out in the presence of a base with or without a solvent. The base can be selected from organic base (e.g., triethylamine, isopropylethylamine, diisopropylamine, pyridine, dimethylaminopyridine, or the like), inorganic base (e.g., sodium hydroxide, potassium hydroxide, sodium carbonate, potassium carbonate, sodium bicarbonate, or potassium bicarbonate), or a mixture thereof. A suitable solvent can be selected from halogenated solvents (e.g., dichloromethane, chloroform, carbon tetrachloride, or the like), ketones (e.g., acetone, 2-butanone, methyl isobutyl ketone, methyl ethyl ketone, or the like), esters (e.g., ethyl acetate, methyl acetate, tertiary butyl acetate, or the like), nitriles (e.g., acetonitrile or the like), aprotic polar organic solvents (e.g., dimethyl formamide, dimethyl sulfoxide, dimethyl acetamide, or the like).

The sulfide of Formula IVa can be oxidized to the sulfone of Formula Va. The oxidation can be carried out using procedures generally known to a person of ordinary skill in the art.

For example, the reaction can be carried out using a suitable oxidizing agent in a solvent. A suitable oxidizing agent can be selected from permanganates (such as potassium permanganate or the like), meta-chloro per benzoic acid, sodium hypochlorite, hydrogen peroxide, tertiary butyl hydrogen peroxide, cumene hydroperoxide or oxone (2 $KHSO_5.KHSO_4.K_2SO_4$). The oxidizing agent can be used in the presence of an appropriate catalyst. An appropriate catalyst can be selected from ammonium molybdate or alkali metal tungstate, such as sodium tungstate. The solvent can be selected from halogenated solvents (e.g., dichloromethane, chloroform, carbon tetrachloride, or the like), ketones (e.g., acetone, 2-butanone, methyl isobutyl ketone, methyl ethyl ketone, or the like), esters (e.g., ethyl acetate, methyl acetate, tertiary butyl acetate, or the like) or alcoholic solvent (e.g., methanol, ethanol, 1-propanol or 2-propanol), or a mixture thereof, optionally in the presence of phase transfer catalysts selected from alkyl ammonium halides (e.g., tetrabutyl ammonium bromide, or the like).

The sulfone of Formula Va can be condensed with the aldehyde of Formula VI to give a compound of Formula VIIa. The condensation can be carried out in the presence of a base selected from metal hydroxides (e.g., sodium hydroxide, potassium hydroxide, or the like), metal carbonates (e.g., potassium carbonate, sodium carbonate, cesium carbonate, lithium carbonate, or the like), alkyl lithium (e.g., methyl lithium, n-butyl lithium, or the like), metal alkoxide (e.g., sodium methoxide, sodium ethoxide, sodium propoxide, sodium tertiarybutoxide, potassium methoxide, potassium ethoxide, magnesium t-butoxide, or the like), metal disilazides (e.g., sodium bis(trimethylsilyl)azanide, lithium bis (trimethylsilyl)azanide, or the like) or a mixture thereof in a solvent selected from ethers (e.g., diethylether, tetrahydrofuran, or the like), polar aprotic solvents (e.g., acetonitrile, dimethyl formamide, dimethyl sulfoxide, dimethyl acetamide, or the like) or mixtures thereof.

The process is characterized by the fact that the compound of Formula VIIa formed by the condensation reaction as described above may or may not be isolated.

A compound of Formula VIIa can be deprotected and/or hydrolyzed to give a compound of Formula VIIIa. Deprotection and hydrolysis can proceed under the similar conditions. Deprotection can be carried out by the methods known to person ordinary skill in the art or as described in *Protecting Groups* by Carey & Sundberg. Particularly, the step can be carried out using an acid such as hydrochloric acid, hydrobromic acid, acetic acid or trifluoroacetic acid, or a base such as sodium hydroxide or potassium hydroxide.

A compound of Formula VIIIa can be converted into an amine salt by reacting it with an organic amine in a solvent. As used herein, amine salts refers to salts of primary amine (e.g., methyl amine, ethyl amine, n-propyl amine or n-butyl amine), secondary amine salts (e.g., 2-propyl amine, 2-butyl amine, or the like) or tertiary amine salts (e.g., tertiary butyl amine or the like) or cyclic amine salts (e.g., cyclohexyl amine or the like), morpholine or pyrrolidine. Preferably, amine salt can be selected from primary amine salt, such as methyl amine salt, or tertiary amine salt such as tertiary butyl amine salt. The amine salts can be crystalline, semi crystalline or amorphous in nature. The solvent used in this step can be selected from halogenated solvents (e.g., dichloromethane, chloroform, carbon tetrachloride, or the like), ketones (e.g., acetone, 2-butanone, methyl isobutyl ketone, methyl ethyl ketone, or the like), nitrile (e.g., acetonitrile or the like), esters (e.g., ethyl acetate, methyl acetate, tertiary butyl acetate, or the like) or alcoholic solvent (e.g., methanol, ethanol, 1-propanol or 2-propanol) or mixtures thereof.

An amine of Formula VIIIa can be converted into a HMG-CoA reductase inhibitor, rosuvastatin calcium thereof using the conditions known to a person ordinary skill in the art. For example, the procedures described in U.S. Pat. No. 5,260,440, WO 2004/014872; WO 2004/108691; WO 2005/042522; WO 2005/054207; WO 2005/077916; WO 2006/035277; WO 2007/041666; WO 2007/125547 or WO 2008/044243. Particularly, using the procedures described in this application.

Having thus described the invention with reference to the particular preferred embodiment and illustrative examples, those in the art can appreciate the modifications to the invention as described and illustrated that do not depart from the spirit and the scope of the invention as disclosed in the specifications. The examples are set forth to aid the understanding of the invention but are not intended to and should not be construed to limit its scope in any way.

Starting Materials
Preparation of Tert-Butyl 3,5-Dideoxy-2,4-O-(1-Methylethylidene)-L-Erythro-Hexuronate tert-Butyl 2,4-dideoxy-3,5-O-(1-methylethylidene)-D-erythro-hexonate (commercially available; 20 g) was added to a pre cooled (0° C. to 5° C.) mixture of 2,2,6,6-tetramethylpiperidine-1-oxyl (0.04 g), potassium bromide (1.92 g), and sodium bicarbonate (18 g) in dichloromethane (120 mL) and stirred at 0° C. to 5° C. for 15 minutes. Aqueous sodium hypochlorite (10%; 40 mL) was added slowly to the resulting mixture and stirred at 0° C. to 5° C. for 30 minutes. Sodium bicarbonate (18 g) was added to the mixture and stirred at 0° C. to 5° C. for 10 minutes, followed by the slow addition of aqueous sodium hypochlorite (10%; 40 ml) in 30 minutes at 0° C. to 5° C. The reaction mixture was stirred at 0° C. to 5° C. for 30 minutes. After completion of the reaction, the reaction mixture was filtered through hyflo bed and washed with dichloromethane (20 mL). The filtrate was washed with aqueous sodium thiosulphate (10%; 100 mL). The organic layer was separated and washed with de-ionized water (100 mL) and finally washed with aqueous solution of sodium chloride (10%; 100 mL). The organic layer was separated and concentrated under vacuum at 40° C. to give tert-butyl 3,5-dideoxy-2,4-O-(1-methylethylidene)-L-erythro-hexuronate.
Dry weight: 19.2 g.

EXAMPLES

Example 1

N-[4-(4-Fluorophenyl)-5-{[(5-Methyl-1,3,4-Thiadiazol-2-Yl)Sulfanyl]Methyl}-6-(Propan-2-Yl)Pyrimidin-2-Yl]-N-Methylmethanesulfonamide Diisopropyl ethyl amine (84.12 g) was slowly added to a mixture of N-[4-(4-fluorophenyl)-5-(hydroxymethyl)-6-(propan-2-yl)pyrimidin-2-yl]-N-methylmethanesulfonamide (commercially available; 100 g) and dimethyl aminopyridine (5 g) and diphenyl chlorophosphate (123.2 g) in dichloromethane (500 mL) at 0° C. to 5° C. The reaction mixture was stirred for 30 minutes at the same temperature to give [4-(4-fluorophenyl)-2-[methyl(methylsulfonyl)amino]-6-(propan-2-yl)pyrimidin-5-yl]methyl diphenyl phosphate. To this mixture was added 2-mercapto-5-methyl-1,3,4-thiadiazole (41 g) at 0° C. to 5° C. followed by slow addition of diisopropyl ethyl amine (36.5 g). The resultant mixture was stirred for 2 hours at 0° C. to 5° C. After completion of the reaction, the mixture was quenched with de-ionized water (500 mL) and acidified to pH 3.5 using hydrochloric acid (6N). The organic layer was separated and washed with sodium bicarbonate (5%) at room temperature. The organic layer was separated and dichloromethane was recovered at 45° C. to give oily residue. Methanol (300 mL) was added to resulting oily residue and the mixture was stirred at room temperature for one hour to give N-[4-(4-fluorophenyl)-5-{[(5-methyl-1,3,4-thiadiazol-2-yl)sulfanyl]methyl}-6-(propan-2-yl)pyrimidin-2-yl]-N-methylmethanesulfonamide, which was filtered, washed with methanol (100 mL) and dried at 45° C. for 2 hours.
Dry Weight: 115 g

Example 2

N-[4-(4-Fluorophenyl)-5-{[(5-Methyl-1,3,4-Thiadiazol-2-Yl)Sulfonyl]Methyl}-6-(Propan-2-Yl)Pyrimidin-2-Yl]-N-Methylmethane sulfonamide Ammonium molybdate (26.5 g) was added to a mixture of N-[4-(4-fluorophenyl)-5-{[(5-methyl-1,3,4-thiadiazol-2-yl)sulfanyl]methyl}-6-(propan-2-yl)pyrimidin-2-yl]-N-methylmethanesulfonamide (Example 1; 100 g), tetra butyl ammonium bromide (5 g) and hydrogen peroxide (30%; 600 mL) in dichloromethane (200 mL) at 0° C. to 5° C. The mixture was stirred for 10 hours to 12 hours at 0° C. to 5° C. After the completion of the reaction, the dichloromethane layer was separated and washed with aqueous solution of sodium metasulfite (2%; 500 mL). The dichloromethane layer was again separated and washed with aqueous solution of sodium bicarbonate (5%; 500 mL) and stirred for 10 minutes. The dichloromethane layer was finally separated and recovered under vacuum at 35° C. to 45° C. to give a residue. Methanol (300 mL) was added to the resulting residue and stirred at room temperature to give N-[4-(4-fluorophenyl)-5-{[(5-methyl-1,3,4-thiadiazol-2-yl)sulfonyl]methyl}-6-(propan-2-yl)pyrimidin-2-yl]-N-methylmethanesulfonamide, which was filtered, washed with methanol (100 mL) and dried under vacuum at 45° C. for 2 hours.
Dry weight: 100 g

Example 3

Tert-Butyl[(4R,6S)-6-{(E)-2-[4-(4-Fluorophenyl)-2-[Methyl(Methylsulfonyl)Amino]-6-(Propan-2-Y1)Pyrimidin-5-Yl]Ethenyl}-2,2-Dimethyl-1,3-Dioxan-4-Yl]Acetate Lithium bis(trimethylsilyl)azanide in terahydrofuran (23% w/w; 268 mL) was added to a pre cooled mixture of N-[4-(4-fluorophenyl)-5-{[(5-methyl-1,3,4-thiadiazol-2-yl)sulfonyl]methyl}-6-(propan-2-yl)pyrimidin-2-yl]-N-methylmethanesulfonamide (Example 2; 100 g) and tert-butyl 3,5-dideoxy-2,4-O-(1-methylethylidene)-L-erythro-hexuronate (54.4 g) in tertahydrofuran (800 mL) at −60° C. to −70° C. After the completion of the reaction, the mixture was washed with saturated aqueous solution of ammonium chloride and the temperature is allowed to rise to 20° C. to 25° C. The reaction mixture was extracted twice with ethylacetate (250 mL+150 mL). The combined ethylacetate layers were washed with aqueous solution of sodium bicarbonate (5%; 500 mL) and brine (500 mL). The organic layer was separated and concentrated under vacuum at 40° C. to 45° C. to give residue. Methanol (700 ml) was added to the resulting residue and stirred at 20° C. to 25° C. for 2 hours. The product was filtered, washed with methanol (100 mL) and dried at 40° C. to 45° C. for 4 hours to 5 hours.
Dry weight: 52.4 g Alternate Method for Tert-Butyl [(4R,6S)-6-{(E)-2-[4-(4-Fluorophenyl)-2-[Methyl(Methylsulfonyl)Amino]-6-(Propan-2-Y1)Pyrimidin-5-Yl]Ethenyl}-2,2-Dimethyl-1,3-Dioxan-4-Yl]Acetate Sodium methoxide (12.8 g) was added in lots to a pre cooled mixture of N-[4-(4-fluorophenyl)-5-{[(5-methyl-1,3,4-thiadiazol-2-yl)sulfonyl]methyl}-6-(propan-2-yl)pyrimidin-2-yl]-N-methylmethanesulfonamide (100 g) and tert-butyl 3,5-dideoxy-2,4-O-(1-methylethylidene)-L-erythro-hexuronate (60 g) in tertahydrofuran (500 mL) at −15° C. to 10° C. After the completion of the reaction, the mixture was quenched with saturated aqueous solution of ammonium chloride. To the resultant mixture, dichloromethane (500 mL) was added and the pH of the mixture was adjusted to 5.0 to 7.0 using dilute hydrochloric acid (2N). The organic layer was washed with aqueous solution of sodium bicarbonate (5%; 200 mL). The organic layer was separated and concentrated under vacuum at 40° C. to 45° C. to give residue. Methanol (1000 mL) was added to the resulting residue and stirred at 20° C. to 25° C. for 2 hours. The product was filtered, washed with methanol (100 mL) and dried at 40° C. to 45° C. for 4 hours to 5 hours.
Dry weight: 60 g

Example 4

(3R,5S,6E)-7-[4-(4-Fluorophenyl)-2-[Methyl(Methylsulfonyl)Amino]-6-(Propan-2-Y1)Pyrimidin-5-Yl]-3,5-Dihydroxyhept-6-Enoic Acid-2-Methylpropan-2-Amine (1:1)

Hydrochloric acid (2 N; 60 mL) was added to a solution of tert-butyl [(4R,65)-6-{(E)-2-[4-(4-fluorophenyl)-2-[methyl(methylsulfonyl)amino]-6-(propan-2-yl)pyrimidin-5-yl]ethenyl}-2,2-dimethyl-1,3-dioxan-4-yl]acetate (Example 3; 50 g) in acetonitrile (500 mL) at room temperature and stirred at the same temperature for 3 hours. After completion of the reaction, aqueous solution of sodium hydroxide (10%; 90 mL) was added to the reaction mixture at room temperature and the temperature of the mixture was allowed to rise to 40° C. to 45° C. The pH of the reaction mixture was adjusted to 12 to 12.8 using aqueous solution of sodium hydroxide (10%). Acetonitrile was recovered completely under vacuum at 45° C. to 50° C. De-ionized water (250 mL) was added to the resulting residue at room temperature. Methyl tert-butyl ether (200 mL) was added to the mixture and stirred for 10 minutes. Layers were separated and methyl tert-butyl ether (200 mL) was added to the aqueous layer and stirred for 10 minutes. Layers were separated and aqueous layer was cooled to 5° C. to 10° C. and adjusted to a pH of 3.5 to 4.0 using hydrochloric acid (2N). Dichloromethane was added to the resulting mixture and stirred for 10 minutes to 15 minutes. Dichloromethane was recovered completely under vacuum at 35° C. to 40° C. Acetonitrile (500 mL) was added to the resulting residue and mixture was cooled to 0° C. to 5° C. To this cooled layer, tert-butyl amine (7 g) was slowly added for 30 minutes at 0° C. to 5° C. and stirred for 2 hours at 10° C. to 15° C. The product was filtered, washed with acetonitrile (50 mL) and dried under vacuum at 45° C. for 3 hours.
Dry weight: 40 g Alternate Method:

Hydrochloric acid (0.02 N; 15 mL) was added to a solution of tert-butyl (3R,5S,6E)-7-[4-(4-fluorophenyl)-2-[methyl(methylsulfonyl)amino]-6-(propan-2-yl)pyrimidin-5-yl]-3,5-dihydroxyhept-6-enoate (Example 3; 15 g) in acetonitrile (150 mL) at 25° C. to 30° C. and stirred at the same temperature for 2 hours. After completion of the reaction, aqueous solution of sodium hydroxide (1.55 g in 30 mL) was added to the reaction mixture at 25° C. to 30° C. and stirred for 2.0 hours at 30° C. to 35° C. Acetonitrile was recovered completely under vacuum at 40° C. to 45° C. De-ionized water (30 mL) was added to the resulting residue at room temperature. Methyl tert-butyl ether (30 mL) was added to the mixture and stirred for 10 minutes. Layers were separated; methyl tert-butyl ether (30 mL) was added to the aqueous layer and stirred for 10 minutes. Layers were separated; the aqueous layer was cooled to 0° C. to 5° C. and added acetonitrile (75 ml) and sodium chloride (25 g) adjusted pH of 3.5 to 4.0 using hydrochloric acid (2N) at 0° C. to 5° C. Organic layer was separated and cooled to 0° C. to 5° C. To this pre-cooled organic layer, tert-butyl amine (1.9 g) was slowly added in 20 minutes at 0° C. to 5° C. and stirred for 1 hour at room temperature. The resulting mixture was cooled to 5° C. to 10° C., filtered, washed with acetonitrile (30 mL) and dried under vacuum at 40° C. to 45° C. for 4 hours.
Dry weight: 12 g Example 5

Rosuvastatin Calcium

Aqueous solution of sodium hydroxide (0.72 g in 10 mL) was added to a solution of (3R,5S,6E)-7-[4-(4-fluorophenyl)-2-[methyl(methylsulfonyl)amino]-6-(propan-2-yl)pyrimidin-5-yl]-3,5-dihydroxyhept-6-enoic acid-2-methylpropan-2-amine (10 g) in de-ionized water (50 mL) at room temperature and stirred for 2 hours to 3 hours at 20° C. to 30° C. The reaction mixture was extracted twice with methyl tertiary butyl ether (2×40 mL) at room temperature. The pH of aqueous layer was adjusted to 9.1 using hydrochloric acid (2N). Residual solvents were recovered under vacuum at 35° C. to 45° C. (~10 mL). The mixture was filtered through 0.45 micron paper and the filtrate was preserved. The filtrate was slowly added in 20 minutes to a solution of calcium acetate (1.99 g) in de-ionized water (20 mL) at room temperature. The resulting mixture was stirred at room temperature for one hour, filtered, washed with de-ionized water (20 mL) and dried under vacuum at 45° C.
Dry Weight: 8.0 g
HPLC purity (%): 99.8

We claim:
1. A process for the preparation of a compound of Formula IVa

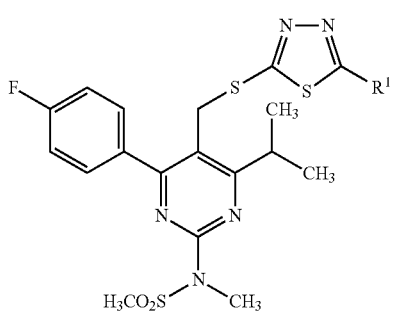

Formula IVa wherein, $R^1$ is hydrogen, $C_1$-$C_4$ alkyl, halogen, nitro, hydroxy, or $C_1$-$C_4$ alkoxy; such process comprising the steps of:

(a) converting a compound of Formula Ia

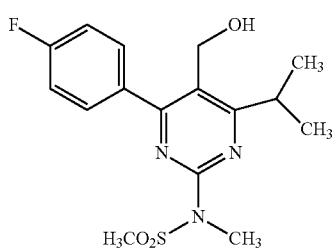

Formula Ia to a compound of Formula IIa,

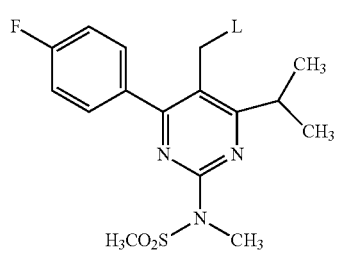

Formula IIa wherein, L is a leaving group; and
(b) reacting a compound of Formula IIa with a compound of Formula III

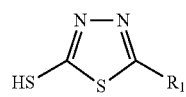

Formula III to give a compound of Formula IVa.

2. A process for the preparation of a compound of Formula Va

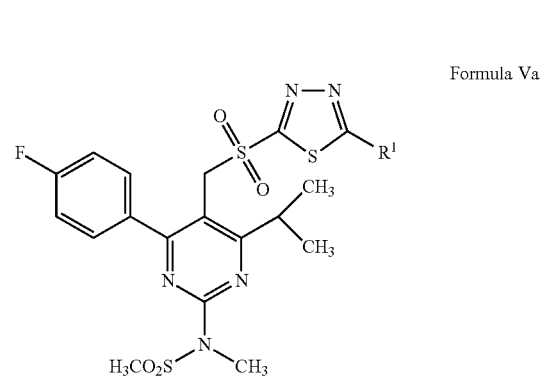

Formula Va wherein $R^1$ is hydrogen, $C_1$-$C_4$ alkyl, halogen, nitro, hydroxy or $C_1$-$C_4$alkoxy, such process comprising the steps of:

(a) converting a compound of Formula Ia

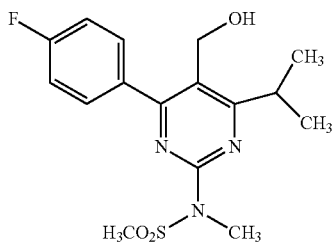

Formula Ia to a compound of Formula IIa,

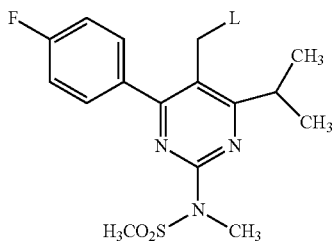

Formula IIa wherein, L is a leaving group;
(b) reacting a compound of Formula IIa with a compound of Formula III

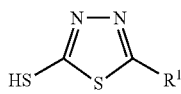

Formula III to give a compound of Formula IVa, and

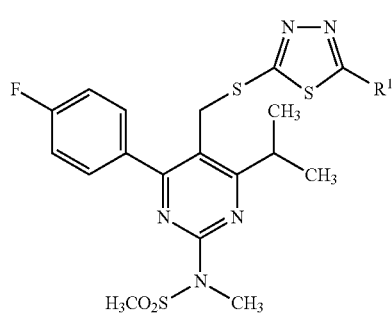

Formula IVa c) oxidizing a compound of Formula IVa to a compound of Formula Va.

3. A compound of Formula IVa or a compound of Formula Va.

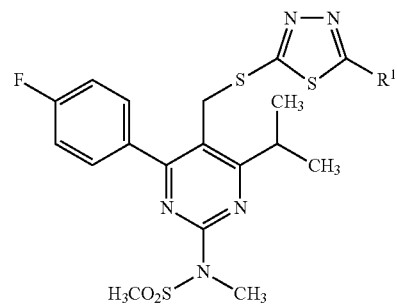

Formula IVa

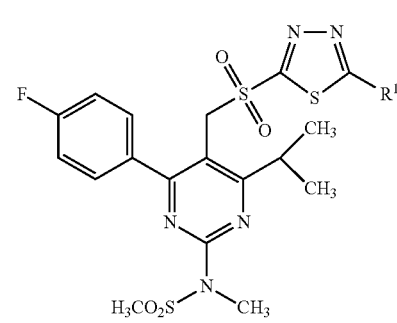

Formula Va

4. A process for the preparation of rosuvastatin calcium of formula

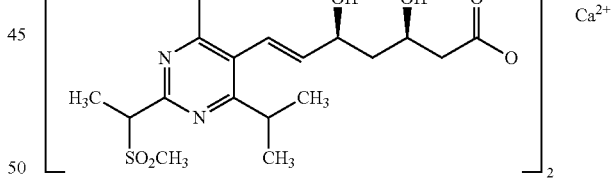

comprising the steps of:
(a) converting a compound of Formula Ia

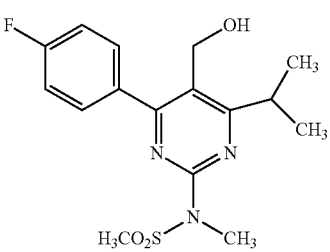

Formula Ia to a compound of Formula IIa;

Formula IIa wherein 'L' is a leaving group (b) reacting a compound of Formula IIa with a compound of Formula III Formula III to give a compound of Formula IVa;

Formula IVa (c) oxidizing a compound of Formula IVa to a compound of Formula Va;

Formula Va (d) condensing a compound of Formula Va with a compound of Formula VI, Formula VI wherein $R^3$ is alkyl, cycloalkyl, arylalkyl, aryl or carbonylbenzyloxy (cbz); $P^1$ and $P^2$ are hydrogen or a protecting group, wherein, $P^1$ and $P^2$ combines to form structure represented as wherein, $R^4$ and $R^5$ is alkyl group, alkoxy group or can combine together to form a cyclic hydrocarbon chain or a carbonyl group, to give a compound of Formula VIIa;

Formula VIIa (e) de-protecting or hydrolyzing a compound of Formula VIIa to give a compound of Formula VIIIa;

Formula VIIIa (f) converting a compound of Formula VIIIa to an amine salt; and
(g) converting an amine salt of a compound of Formula VIIIa to rosuvastatin calcium.

5. The process according to claim 4, wherein 'L' is leaving group selected from a group consisting of alkyl sulphonyloxy, aryl suphonyloxy, phosphate or phosphite groups.

6. The process according to claim 5, wherein 'L' is diphenyl phosphate.

7. The process according to claim 4, wherein $R^1$ is $C_1$-$C_4$ alkyl.

8. The process according to claim 4, wherein the step (b) is reacted in the presence of a base selected from triethylamine, diisopropylethylamine, diisopropylamine, pyridine or dimethylaminopyridine.

9. The process according to claim 8, wherein an organic base is diisopropylethylamine.

10. The process according to claim 4, wherein the step (c) is performed using an oxidizing agent selected from a group consisting of permanganates, meta-chloro per benzoic acid, sodium hypochlorite, hydrogen peroxide, tert-butyl hydrogen peroxide, cumene hydroperoxide or oxone ($2KHSO_5 \cdot KHSO_4 \cdot K_2SO_4$) in the presence of transition metal catalysts.

11. The process according to claim 10, wherein oxidation is performed using hydrogen peroxide in the presence of ammonium molybdate.

12. The process according to claim 4, wherein $P^1$ and $P^2$ are acetonide (isopropylidene) group.

13. The process according to claim 4, wherein an amine salt is selected from a group consisting of methyl amine, ethyl amine, n-propyl amine, isopropyl amine, n-butyl amine or tert-butyl amine.

14. The process according to claim 13, wherein an amine salt is tert-butyl amine salt.

15. The process according to claim 4, wherein an amine salt is treated with a base and then converted to rosuvastatin calcium by treatment with calcium hydroxide.

* * * * *